(12) United States Patent
Charrad et al.

(10) Patent No.: US 10,424,237 B2
(45) Date of Patent: Sep. 24, 2019

(54) ASSIGNING DIFFERENT APPLICATION PROGRAMS OF A MEDICAL IMAGING APPARATUS TO DETECTED DISPLAY DEVICES

(71) Applicant: Siemens Healthcare GmbH, Erlangen (DE)

(72) Inventors: Chiheb Charrad, Neunkirchen A. Brand (DE); Ivan Murphy, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/846,676

(22) Filed: Dec. 19, 2017

(65) Prior Publication Data

US 2018/0182281 A1 Jun. 28, 2018

(30) Foreign Application Priority Data

Dec. 22, 2016 (EP) .................................... 16206397

(51) Int. Cl.
*G09G 5/00* (2006.01)
*G09G 3/20* (2006.01)
(Continued)

(52) U.S. Cl.
CPC .......... *G09G 3/2092* (2013.01); *A61B 5/055* (2013.01); *A61B 6/464* (2013.01); *A61B 6/502* (2013.01);
(Continued)

(58) Field of Classification Search
None
See application file for complete search history.

(56) References Cited

U.S. PATENT DOCUMENTS 9,955,288 B2 * 4/2018 Kim ........................ G06F 3/147
2003/0231143 A1 * 12/2003 Nakamura ............ G06F 3/1423
345/1.1
(Continued)

FOREIGN PATENT DOCUMENTS

WO WO-20140162054 A1 10/2014

OTHER PUBLICATIONS

Office Action issued by the European Patent Office dated Sep. 11, 2018 for EP Application No. 16206397.8.

*Primary Examiner* — Martin Mushambo
(74) *Attorney, Agent, or Firm* — Harness, Dickey & Pierce, P.L.C.

(57) ABSTRACT

A method is for operating a medical imaging system including at least two executable application programs. An embodiment includes: a) a computing device of the imaging system detecting at least one display device by its properties relevant to visual display; b) the computing device retrieving at least one particular application-specific requirement made of a display device, using the at least two application programs, for visual display of corresponding application program information on a display device; c) comparing the properties detected for each at least one display device and the retrieved requirement; and d) according to a result of the comparison, the computing device either assigning the application programs respectively to the at least one display device or activating an assignment facility for a user, to increase efficiency when operating the medical imaging system having the at least two executable application programs in a manner convenient to a user.

23 Claims, 1 Drawing Sheet

(51) Int. Cl.
  *G16H 40/63* (2018.01)
  *A61B 5/055* (2006.01)
  *A61B 6/00* (2006.01)
  *A61B 8/00* (2006.01)
  *G06F 3/14* (2006.01)

(52) U.S. Cl.
  CPC ............... *A61B 8/464* (2013.01); *G06F 3/14* (2013.01); *G16H 40/63* (2018.01); *G09G 2320/0613* (2013.01); *G09G 2340/0407* (2013.01); *G09G 2340/0435* (2013.01); *G09G 2340/0464* (2013.01); *G09G 2340/0492* (2013.01); *G09G 2340/06* (2013.01); *G09G 2340/145* (2013.01); *G09G 2360/04* (2013.01); *G09G 2370/22* (2013.01); *G09G 2380/08* (2013.01)

(56) References Cited

U.S. PATENT DOCUMENTS

| | | | |
|---|---|---|---|
| 2005/0190203 A1* | 9/2005 | Gery | G06F 9/451 345/660 |
| 2006/0117253 A1* | 6/2006 | Polash | G06F 17/211 715/247 |
| 2009/0119182 A1* | 5/2009 | Krstulich | G06F 21/42 705/26.1 |
| 2009/0160731 A1* | 6/2009 | Schuler | G06F 3/1423 345/1.1 |
| 2011/0037711 A1* | 2/2011 | Siddiqui | G06F 3/1423 345/173 |
| 2012/0038550 A1* | 2/2012 | Lemmey | G06F 3/017 345/156 |
| 2014/0258918 A1* | 9/2014 | Morishima | A61B 6/463 715/783 |
| 2015/0091778 A1* | 4/2015 | Day | G06F 3/1446 345/1.3 |
| 2015/0130685 A1* | 5/2015 | Kim | G06F 3/147 345/3.1 |
| 2015/0149529 A1* | 5/2015 | Loader | G06F 9/542 709/203 |
| 2016/0048299 A1* | 2/2016 | Sirpal | G06F 1/1616 715/761 |
| 2017/0337027 A1* | 11/2017 | Chan | G06F 3/0481 |
| 2018/0182281 A1* | 6/2018 | Charrad | G16H 40/63 |

\* cited by examiner

FIG 1

FIG 2

ASSIGNING DIFFERENT APPLICATION PROGRAMS OF A MEDICAL IMAGING APPARATUS TO DETECTED DISPLAY DEVICES

PRIORITY STATEMENT

The present application hereby claims priority under 35 U.S.C. § 119 to European patent application number EP 16206397.8 filed Dec. 22, 2016, the entire contents of which are hereby incorporated herein by reference.

FIELD

At least one embodiment of the invention generally relates to a method for operating a medical imaging system having at least two executable application programs.

BACKGROUND

In medical imaging, one of the keys to a working environment that allows standardized, convenient and efficient working at different workstations is to provide a generic user interface that can display (or host) application program information from the various application programs irrespective of the application program currently in use. In this context, each application program is typically developed for one or more workflow runs within a branch of medical imaging, for instance magnetic resonance imaging or ultrasound imaging. It is often required here to use different application programs at one workstation in order to run through efficiently the different tasks of the daily workflows in medical imaging, for instance image acquisition or image postprocessing.

Typically, the users start the required application programs individually on a suitable computing device, and then switch to and fro manually between the various application programs with recourse to the properties and capabilities of an operating system of the computing device. Not only is this solution not user-friendly but it also encourages numerous mistakes. For instance, when switching over manually, the user can easily overlook a workflows step or, for example, when working in parallel with different instances of the various application programs, which are each associated with different patients, the user can also confuse the instances, resulting in a mixup between patients or patient data.

In order to provide better support to the user, there are systems that integrate the user interfaces of different application programs in one standardized user interface, what is known as a user interface (UI) container. Different applications are thereby able to use available input and/or output devices by elements being inserted into the user interface that can be used to bring to front the application programs currently required according to the workflow, or by these elements assigning to the different application programs respective display areas on a suitable display device in a predetermined manner. Even this improved approach, however, is not sufficient for providing user-friendly and efficient support for the various imaging workflows that a user runs through at a workstation in a day with different patients.

In other approaches, the application programs and the input and output devices are configured in a manufacturing process before delivery to a user. This accordingly involves assigning the appropriate devices, i.e. input and/or output devices, permanently to one or more application programs. It is possible to modify such an assignment or configuration in this case by adapting the user interface, although this must be performed by a trained person who knows what requirements are made of the relevant input and/or output devices by the respective application programs or applications, because not every application program can deliver the desired medical results using every delivered display device.

SUMMARY

At least one embodiment of the invention increases the efficiency when operating a medical imaging system having at least two executable application programs in a manner convenient to a user, and in at least one embodiment, reduces the frequency of mistakes during operation of the medical apparatus.

Independent claims, the description and the figures contain advantageous embodiments.

At least one embodiment of the invention relates to a method for operating a medical imaging system having at least two executable application programs. The executable application programs may be computer programs, for example. The application programs in particular are independent of one another, i.e. can also be executed singly. For example, they serve a different purpose or a different function in the imaging system, so for instance image acquisition, i.e. capturing an image, or postprocessing, i.e. editing an acquired image.

At least one embodiment of the invention relates to a method for operating a medical imaging system having at least two executable application programs. In an example embodiment, the method comprises:

a) a computing device of the imaging system detecting at least one display device by its properties relevant to visual display;

b) the computing device retrieving at least one particular application-specific requirement made of a display device by the at least two application programs for visual display of corresponding application program information on a display device;

c) comparing the properties detected in each case for the at least one display device and the retrieved requirement;

d) according to a result of the comparison, the computing device either assigning the application programs respectively to the at least one display device or activating an assignment facility for a user.

At least one embodiment of the invention also relates to a medical imaging system having at least two executable application programs, which system comprises a computing device that is designed to: a) detect at least one display device by its properties relevant to visual display; b) retrieve at least one particular application-specific requirement made of a display device by the at least two application programs for visual display of corresponding application program information from the respective application programs on a display device; c) compare the properties detected in each case for the at least one display device with the retrieved requirement; and d) according to a result of the comparison, either assign the application programs respectively to the at least one display device or activate an assignment facility for a user. When there are a plurality of display devices, the computing device can be designed to assign a different display device to each application program.

The features and feature combinations mentioned above in the description, and the features and feature combinations mentioned below in the description of the figures and/or shown solely in the figures can be used not just in the particular combination stated but also in other combinations without departing from the scope of the present invention. The invention shall therefore be deemed to include and disclose also embodiments that are not described and shown explicitly in the figures but can be derived and produced from the described embodiments by separate feature combinations. Embodiments and feature combinations that hence do not comprise all the features of an independent claim in the original wording shall also be deemed to be disclosed. Furthermore, embodiments and feature combinations that go beyond or differ from the feature combinations presented in the dependency references of the claims shall be deemed to be disclosed, in particular by the embodiments described above.

BRIEF DESCRIPTION OF THE DRAWINGS

Example embodiments of the invention are explained in more detail below with reference to a schematic drawing, in which.

The same reference numbers are used to denote identical or equivalent elements.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, the method comprises a plurality of method steps. One method step is detecting at least one display device, which can also be referred to as a visual output device, by its particular properties relevant to visual display or output of information. It is also possible to detect just one single property here. In this case, the display device is accordingly detected by at least one relevant property. A computing device of the imaging system performs the detection.

A further method step is the computing device retrieving at least one particular application-specific requirement made of a display device by the at least two application programs for visual display of corresponding application program information on the respective display devices. Hence the computing device retrieves an application-specific requirement for each application program. The application-specific requirements can be retrieved, for example, in the form of an application profile of the particular application program.

The requirements can also contain the information that the application program makes no (specifically noteworthy) requirement of the display device. The requirement can also comprise a minimum requirement and/or an optimum requirement. The requirement can be stored in the imaging system. The requirement can also be retrieved for an application program on the basis of the category or the purpose of use of the application program or can be defined by the computing device. So for instance, application programs designed for a mammography system as an imaging system typically need two high resolution monitors in portrait format, whereas applications for a simple computed tomography system as a medical imaging system typically require only one single monitor in landscape format, possibly also a touch-sensitive monitor.

Application programs for a high-quality magnetic resonance imaging system in turn generally require two landscape-format monitors for an optimum and efficient workflow. In addition, a user can also add an extra monitor to the particular system according to personal requirements, for instance for a radiology information system (RIS) running in parallel with other application programs, or for a work list or to-do list, which accompanies a workflow for instance. This can also be stored, for example, in a requirement profile as an application-specific requirement.

A further method step is the computing device comparing the property (properties) detected in each case for the at least one display device and the retrieved application-specific requirement(s). The properties and requirements each by definition relate to the same parameters. Hence it is possible to compare, for example, a required minimum resolution for a mammography application program with an available maximum resolution of a detected display device.

A next method step is then the computing device, according to a result of the comparison, assigning the application programs respectively to the at least one display device, or activating an assignment facility for a user. For instance in this case, the at least one detected display device can display to the user an assignment facility. It is hence possible, for example, to assign automatically to an application program the display device that satisfies the relevant requirement profile, i.e. the application-specific requirement, or can deliver the best medical results. It is also possible in this case, for example, to assign a relevant display area or image area of the at least one display device to the particular application program(s).

As a further method step, it is also possible to display corresponding application-program information of the application program on the at least one display device assigned to the particular application program.

This has the advantage that the user interface can be adapted optimally for each of the application programs to the at least one display device and its particular technical capabilities. In this process, the application programs do not themselves need any information about the display device or display devices, because the computing device can perform the coordination of the visual display of the application program information of the respective application programs, i.e. the "display management". It can thereby be guaranteed that the user interface satisfies the relevant requirements of the application programs and of the particular medical scenario irrespective of a configuration given at the time the system was produced.

The application programs hence do not need to know the hardware, i.e. the display devices, whereas the system or the computing device knows from the retrieved application-specific requirements that, for example, a mammography application program needs a high resolution screen or a high resolution display device, and can use the device if it is present and is detected. If a high resolution display device is not detected, or possibly the system detects a plurality of suitable display devices, or for other reasons cannot decide which display device is meant to be assigned to the relevant application program, the system can ask the user by activating the assignment facility for the user, and the user can make the decision. In this case, the relevant user input in particular can be saved and, as a new application-specific requirement, can overwrite or augment, for example, a factory setting or manufacturer setting, and be used as an application-specific requirement when the method is performed in future.

An imaging system that works using the described method hence can be used flexibly in numerous different usage scenarios. The system can be implemented using the application programs with little effort on different hardware implementations, because the various application programs do not need to be adapted to suit the possible hardware configuration of the system. Thus, for example, a platform for the medical imaging system can be provided that can be adapted by different parties, for instance by an end-user or even by a reseller, using different hardware in each case to suit personal requirements, and operated with the same application programs.

An advantageous embodiment provides that the assignment includes allocating different display areas of the at least one display device, i.e. of one or more display devices, to the various application programs. Different display areas of a single display device, or else different display areas of different display devices, can hence be assigned to the different application programs. In particular, the display areas available in one display device can be allocated entirely to a particular application program, with the result that application program information only from a single application program is displayed on one display device at a time.

This has the advantage of creating a particularly clear working environment. For instance, the application programs can hence each be assigned to different windows on one display device, or else to one full-screen image on a display device. This can be done, for example, by the means used when operating a computer using a web browser that allows different tabs of a web browser to be resolved manually into windows which can then be arranged in any position on one or more display devices.

This has the advantage of achieving a particularly flexible presentation. The described method allows automatic calculation and appropriate scaling of the application program information to be displayed to fit the allocated display areas or the assigned display device. Since the various display devices can differ significantly in terms of greater resolution and in terms of other properties, it is thereby possible to make better use of a display potential of the medical system.

Another advantageous embodiment provides that a plurality of display devices are detected. In particular in this case, at least two display devices differ from the plurality of display devices in terms of their properties relevant to the visual display.

Especially when there are a plurality of display devices, detecting the display devices and appropriate application-specific assignment of the display devices to the application programs on the basis of their properties results in a particularly large increase in efficiency and convenience. This applies especially to display devices having different properties.

Another advantageous embodiment provides that the at least one detected display device, in particular one, or preferably all, of a plurality of detected display devices is in each case a screen or a touchscreen or a 3D screen for three-dimensional depiction of images or a projector or a pair of smartglasses, preferably a pair of smartglasses for virtual and/or augmented reality or another type of display device.

The described method is particularly advantageous for the display devices mentioned because although some of them have distinctly different properties they may all be used in a medical scenario by an imaging system. In this case, the described method makes it particularly easy to exploit the various properties in order to work efficiently with the system.

Another advantageous embodiment provides that the detected property and respectively the retrieved requirement comprises or relates to one or more of the following parameters of the particular display devices or of the particular application program: a displayable or respectively required or recommended image resolution; a displayable or respectively required or recommended frame rate; a displayable or respectively required or recommended color space; calibration information; an existing or respectively recommended or required size of a display surface, an existing or respectively recommended or required orientation, i.e. for example a horizontal or vertical orientation or main direction of extension, of the display surface; arrangement information, for instance regarding the arrangement of a display device relative to another display device of the plurality of display devices; type information, which in particular indicates whether the particular display device is a conventional screen or a touchscreen or a 3D screen or a projector or a pair of smartglasses, preferably a pair of smartglasses for virtual and/or augmented reality, or another type of device, or respectively whether a screen or a touchscreen or a 3D screen or a projector or a pair of smartglasses is recommended or required.

The properties mentioned have the advantage that they can be used to ascertain particularly effectively the suitability of the display device for the particular application programs in the medical field, thereby further improving the efficiency of the method and the user-friendliness.

An example embodiment provides that the method is performed automatically during a start-up procedure or during bootup of the medical imaging system. Thus for instance a manufacturer can specify a standard configuration for the application programs and a plurality of screens or monitors, for instance at least two screens or monitors, wherein two display devices are assigned to different application programs.

In this case, the system can be delivered comprising correspondingly two display devices, and operated in a two-monitor mode. If now, for example, a third-party, whether a user or a reseller, then connects a third display device, then the system automatically detects this device and, for example, switches over to a three-monitor mode for the system comprising the three display devices if this is stored in the requirement profile or in the application-specific requirements. Alternatively, for example, it can hence also be detected if a display device fails. Then, for instance, instead of the application program assigned to the faulty screen and intended for display on the screen simply remaining invisible to a user, which is otherwise normally the case, the user is given the opportunity to assign a different display device to the application program.

This has the advantage that an optimized assignment of application programs and display devices is always achieved irrespective of a status of the imaging system on delivery. Furthermore, the system utilizes in a particularly flexible and user-friendly manner existing capacities for displaying information.

Another advantageous embodiment provides that the application programs belong to different categories, in particular each belongs to one of the categories: planning, for instance planning a work list; image acquisition, for instance scanning a patient or recording an image; postprocessing, for instance postprocessing recorded image data; or presentation, for instance presenting image results to the user of the system or other people.

This has the advantage that for different application programs, relevant application-specific requirements can be retrieved generically without the particular application program being identified specifically. This further increases the flexibility of the system.

Another advantageous embodiment provides that the application programs are suitable for use in an ultrasound system and/or in a mammography system and/or in a computed tomography system and/or in a magnetic resonance system.

In this case, the method has the advantage that the system can be used for different purposes and moreover can adapt itself flexibly to the particular conditions, or more precisely can be adapted for the particular conditions in the various imaging branches such that it adapts itself to the particular use by means of the method described here.

Another advantageous embodiment provides that in the computing device is defined for the application programs at least one workflow, which specifies a time sequence for activating and/or executing the application programs, so for instance simultaneous or successive execution and/or activation of the application programs, and a display of corresponding application program information from the various application programs on the display device assigned to the particular application program.

The workflow can be defined, for example, in the manner that an automatically launched framework program, a master application, activates the application programs of the system according to a specified scheme, or invites the user to activate the application programs. A particular case here is that the application programs can be activated solely via the framework program. In this process, for example, the framework program can allocate on the assigned display device a corresponding display area to the particular application program or the application programs. For a particular workflow, it is also possible here to provide corresponding application-specific requirements for each of the different application programs, for instance for the different categories of application programs.

The application-specific requirements can hence also depend on the workflow. Thus, for example, a specific arrangement or topology of the display devices at the workstation can be stored for a particular workflow. For a different workflow, a different arrangement can be stored. This allows user-specific adaptation of the workflow using corresponding different requirements for the application programs. In this case, certain requirements for the application programs can also be defined in a way that cannot be altered by a user, in order to prevent mistakes in use. At the same time the imaging system can still be customized and adapted to individual requirements. Thus the various application programs can be activated according to the defined workflow in a defined context and assigned to the different display devices.

Accordingly another advantageous embodiment provides that the workflow and hence in particular also the application-program specific requirements can be adapted by a user, and the adapted workflow can be stored in the computing device.

The framework program can thereby provide a framework for the other application programs, in particular including specific user interface elements in order to switch to and fro between the different application programs. The corresponding application programs assigned to the framework program in particular cannot have their own framework in this case, i.e. they can be actuated or activated either automatically, for instance actuated by an event in another application program, and/or automatically or semi-automatically as part of the workflow, for example can be actuated or activated by a configurable or dynamically inserted control of the user interface, for instance a button displayed by the framework program.

This has the advantage that the application programs are assigned to the relevant display devices particularly efficiently and effectively and in a failsafe and user-friendly manner.

Another advantageous embodiment provides that the workflow activates at least one particular instance of the various application programs, which is used to treat at least one particular patient by the medical imaging system, and instances of the various application programs that are used to treat the same patient are labeled as such and/or displayed simultaneously and/or displayed on the adjacent display areas and/or adjacently arranged display devices.

This has the advantage that the user can immediately and easily identify which instances, or which application program information, belong to the same patient in each case. This conveniently prevents incorrect operation or mistakes during treatment of the patient.

At least one embodiment of the invention also relates to a medical imaging system having at least two executable application programs, which system comprises a computing device that is designed to: a) detect at least one display device by its properties relevant to visual display; b) retrieve at least one particular application-specific requirement made of a display device by the at least two application programs for visual display of corresponding application program information from the respective application programs on a display device; c) compare the properties detected in each case for the at least one display device with the retrieved requirement; and d) according to a result of the comparison, either assign the application programs respectively to the at least one display device or activate an assignment facility for a user. When there are a plurality of display devices, the computing device can be designed to assign a different display device to each application program.

Advantages and advantageous embodiments of the medical imaging system or apparatus correspond here to advantages and advantageous embodiments of the described method for operating a medical imaging system.

Figure 1:
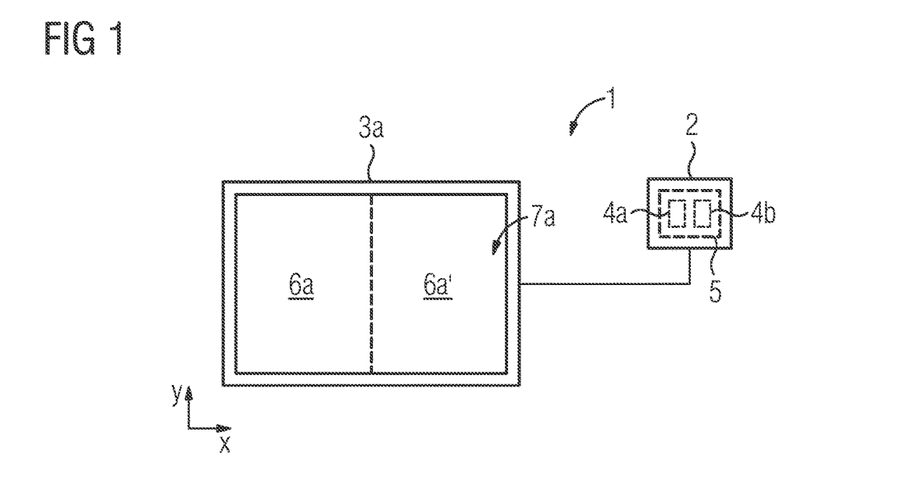
FIG. 1 shows a first example embodiment of a medical imaging system.

FIG. 1 shows an example embodiment of a medical imaging system. The medical imaging system 1 in this case comprises a computing device 2 and a display device 3a. The computing device 2 is designed here to detect the display device 3a by its properties relevant to visual display.

In addition in this case, in the computing device 2 are two application programs 4a, 4b, which can be activated via a framework program 5. The computing device 2 is now also designed to retrieve at least one particular application-specific requirement made by the at least two application programs 4a, 4b of, in general, a display device, in this case the display device 3a, for visual display of corresponding application program information on, in general, a display device, in this case the display device 3a. So, for example, a minimum size or an orientation of a display surface 7a of the display device 3a can be stipulated for the respective application programs 4a, 4b. The computing device 2 is also designed to compare the properties detected for the display device 3a, for instance a screen size, and the retrieved requirement for the two application programs 4a, 4b.

Each of the two application programs 4a, 4b can hence stipulate a specific minimum size of a presentation on the display device 3a. The computed device 2 is also designed, according to a result of the comparison either to assign the application programs 4a, 4b respectively to the display device 3a, or to activate an assignment facility for a user. In the present case, a corresponding display area 6a, 6a' on the display surface 7a of the display device 3a can thus be allocated to the two programs 4a, 4b. If by way of example the particular region meets in terms of its size the requirements of the application programs 4a, 4b then, in the example shown, corresponding application program information from the first application program 4a is displayed in the first display area 6a, and application program information from the second application program 4b is displayed in the second display area 6a' of the display device 3a. If now by way of example the size of the display device is not large enough to satisfy the requirements of the two application programs 4a, 4b, then the user can be prompted accordingly either to provide an additional display device or to allocate the display areas 6a, 6b manually, for instance to split the display surface 7a according to the user's requirements into the display areas 6a, 6b and hence assign image areas of different size to the two application programs 4a, 4b.

Figure 2:
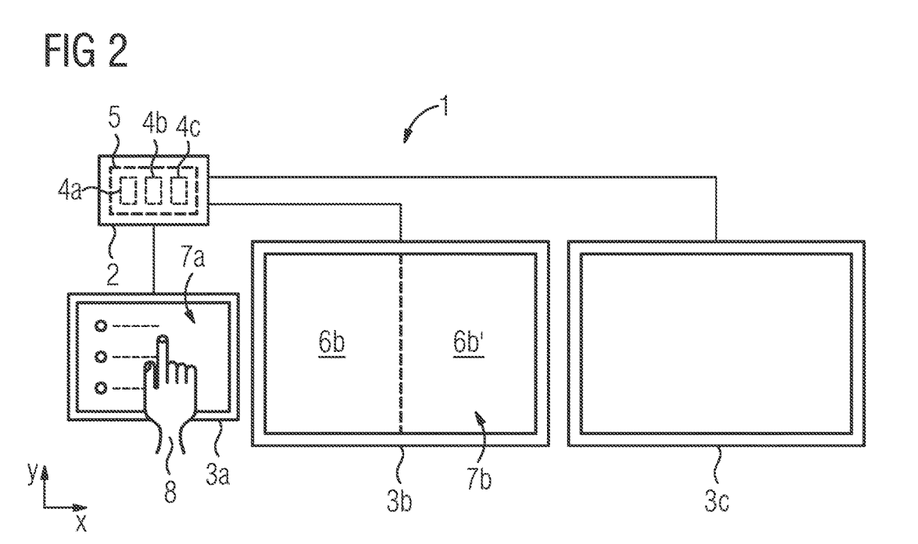
FIG. 2 shows a second example embodiment of a medical imaging system.

FIG. 2 shows another example embodiment of a medical imaging system. In this example, the medical imaging system 1 comprises three display devices 3a, 3b, 3c, of which the first display device 3a is designed as a touch-sensitive display device and hence is designed to double as an input device. The other two display devices 3b, 3c in the present case are screens that extend mainly in the x-direction in landscape format. The computing device 2 is equipped, as in FIG. 1, with a plurality of application programs, in this case three application programs 4a, 4b, 4c, which likewise are activated by the framework program 5.

In the present example, the application programs 4a, 4b, 4c are assigned to different categories, namely the first program 4a is assigned to planning, the second application program 4b to image acquisition, and the third application program 4c to postprocessing. According to the requirements stored for each of the different categories, the computed device 2 now detects the display devices 3a to 3c by their respective properties relevant to the visual display or operation.

Since in this case a touch-sensitive display device is identified as the first display device 3a, the computing device 2 assigns this display device to the first application program 4a, for example. A user 8 can thereby accordingly edit a work list, for instance mark or check off a work list, intuitively on the display surface 7a of the first display device 3a. In the present example, the two other display devices 3b, 3c are conventional display devices and hence are equally suited here for imaging or postprocessing. The second and third display devices 3b, 3c are accordingly assigned to the second and third application programs 4b, 4c respectively in this case. This is all done automatically in this example.

The advantages of the described method include that, for instance, if the third display device 3c is faulty, this is detected by the computing device 2 and hence the third application program 4c can be, or is, assigned also to the second display device 3b. Thus, for instance, respective display areas 6b, 6b' of the display surface 7b of the second display device 6b can be allocated to the different application programs 4b and 4c. In the example shown, this is done only automatically if, as in the example shown in FIG. 1, this is also sensible according to the retrieved application-specific requirements or an active user requirement. This can be implemented, for example, by the display devices 3a, 3b, 3c being detected automatically during bootup and comparing their properties with the application-specific requirements.

This can also achieve greater flexibility, because the third display device 3c may not merely be faulty but may also be removed or added, as a particular user sees fit. Thus, for instance, the imaging system 1 may also be delivered comprising two display devices 3a, 3b and then the additional display device 3c added subsequently, which is then automatically detected and used in the imaging system 1 optimally for the application programs 4a to 4c.

Of course the detected properties and the corresponding application-specific requirements can comprise not just the parameters described here of the size of the display surface 7a, 7b or the parameter of type information, namely whether or not the display element 3a, 3b, 3c is touch sensitive, but may also comprise many other parameters such as, for example, image resolution, frame rate, color space, calibration information, orientation of the display surface 7a, 7b, arrangement information, according to which, for example, the second display device 3b is a central display device in this case.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for a medical imaging system including at least two executable application programs, the method comprising:
   detecting, via a computing device of the imaging system, properties of at least one display device relevant to visual display;
   retrieving, via the computing device, at least one application-specific requirement of the at least two executable application programs based on application profiles associated with respective ones of the at least two executable application programs prior to assigning the at least two executable application programs to the at least one display device, each of the at least one application-specific requirement being a requirement associated with visual display using a respective one of the at least two executable application;
   comparing the properties of each of the at least one display device and the at least one application-specific requirement; and
   assigning, via the computing device, the at least two executable application programs, respectively, to the at least one display device based on a result of the comparing, the at least two executable application programs being executable independently from each other such that the at least two executable application programs are assignable to and independently executable by different ones of the at least one display device without providing the at least two executable application programs with the properties of the at least one display device.

2. The method of claim 1, wherein the assigning includes allocating different display areas of the at least one display device to the at least two executable application programs.

3. The method of claim 2, wherein the detecting includes detecting a plurality of display devices via the computing device, wherein at least two of the plurality of display devices differ in terms of properties relevant to visual display.

4. The method of claim 3, wherein at least one of the plurality of display devices is a screen, a touchscreen, a 3D screen, a projector or a pair of smartglasses.

5. The method of claim 4, wherein, the pair of smartglasses includes a head pair of smartglasses for at least one of virtual and augmented reality.

6. The method of claim 2, wherein the method is performed automatically during a start-up procedure of the medical imaging system.

7. The method of claim 1, wherein the detecting includes detecting a plurality of display devices via the computing device, wherein at least two of the plurality of display devices differ in terms of properties relevant to visual display.

8. The method of claim 7, wherein at least one of the plurality of display devices is a screen, a touchscreen, a 3D screen, a projector or a pair of smartglasses.

9. The method of claim 8, wherein, the pair of smartglasses includes a head pair of smartglasses for at least one of virtual and augmented reality.

10. The method of claim 1, wherein the at least one display device is a screen, a touchscreen, a 3D screen, a projector or a pair of smartglasses.

11. The method of claim 1, wherein the properties relevant to visual display include one or more of:
   a displayable image resolution;
   a displayable frame rate;
   a displayable color space;
   calibration information;
   a size of a display surface;
   an orientation of the display surface;
   arrangement information; and
   type information.

12. The method of claim 11, wherein type information indicates whether the at least one display device is a screen, a touchscreen, a 3D screen, a projector or a pair of smartglasses.

13. The method of claim 12, wherein, the pair of smartglasses includes a head pair of smartglasses for at least one of virtual and augmented reality.

14. The method of claim 1, wherein the method is performed automatically during a start-up procedure of the medical imaging system.

15. The method of claim 1, wherein the at least two executable application programs belong to different ones of planning, imaging, postprocessing or presentation.

16. The method of claim 15, wherein the at least two executable application programs belong to one of categories planning or imaging or postprocessing or presentation.

17. The method of claim 1, wherein the at least two executable application programs are suitable for use in at least one of an ultrasound system, a mammography system, a computed tomography system, and a magnetic resonance system.

18. The method of claim 1, wherein in the computing device is defined, for the at least two executable application programs, at least one workflow, the at least one workflow specifying a time sequence for activating the at least two executable application programs, and a display of corresponding application program information from the at least two executable application programs on the display device assigned to one of the at least two executable application programs.

19. The method of claim 18, wherein the at least one workflow is adaptable by the user, the at least one workflow, once adapted, is configured to be stored in the computing device.

20. The method of claim 18, wherein the at least one workflow is configured to activate at least one instance of at least one of the at least two executable application programs used to treat a patient by the medical imaging system, and wherein at least one instance used to treat the same patient are at least one of labeled, displayed simultaneously, displayed on adjacent display areas and adjacently arranged on display devices.

21. A non-transitory computer readable medium including program code for carrying out the method of claim 1 when the program code is run on a computer.

22. A medical imaging system including at least two executable application programs, the system comprising:
a computing device configured to,
detect properties of at least one display device relevant to visual display;
retrieve at least one application-specific requirement of the at least two executable application programs based on application profiles associated with respective ones of the at least two executable application programs prior to assigning the at least two executable application programs to the at least one display device, each of the at least one application-specific requirement being a requirement associated with visual display using a respective one of the at least two executable application;
compare the properties of each of the at least one display device and the at least one application-specific requirement; and
assign the at least two executable application programs, respectively, to the at least one display device based on a result of comparing the properties, the at least two executable application programs being executable independently from each other such that the at least two executable application programs are assignable to and independently executable by different ones of the at least one display device without providing the at least two executable application programs with the properties of the at least one display device.

23. A medical imaging system including at least two executable application programs, the system comprising:
a first memory storing computer-readable instructions and the at least two executable application programs; and
one or more processors configured to execute the computer-readable instructions to,
detect properties of at least one display device relevant to visual display;
retrieve at least one application-specific requirement of the at least two executable application programs based on application profiles associated with respective ones of the at least two executable application programs prior to assigning the at least two executable application programs to the at least one display device, each of the at least one application-specific requirement being a requirement associated with visual display using a respective one of the at least two executable application;
compare the properties of the at least one display device and the at least one application-specific requirement; and
assign the at least two executable application programs, respectively, to the at least one display device based on a result of comparing the properties, the at least two executable application programs being executable independently from each other such that the at least two executable application programs are assignable to and independently executable by different ones of the at least one display device without providing the at least two executable application programs with the properties of the at least one display device.

* * * * *